United States Patent [19]
Geistert

[11] Patent Number: 6,066,136
[45] Date of Patent: May 23, 2000

[54] ABLATION CATHETER WITH A PLURALITY OF POLES

[75] Inventor: Wolfgang Geistert, Rheinfelden-Herten, Germany

[73] Assignee: Sulzer Osypka GmbH, Grenzach-Wyhlen, Germany

[21] Appl. No.: 09/093,525

[22] Filed: Jun. 8, 1998

[30] Foreign Application Priority Data

Jun. 13, 1997 [EP] European Pat. Off. .............. 97810373

[51] Int. Cl.[7] .................................................. A61B 18/18
[52] U.S. Cl. ........................... 606/41; 607/122; 607/101; 600/374
[58] Field of Search ........................... 606/45–50, 41–42, 606/34, 32–35, 37–40; 607/122, 101, 102, 115, 116; 600/374, 508, 509

[56] References Cited

U.S. PATENT DOCUMENTS

| | | |
|---|---|---|
| 4,945,912 | 8/1990 | Langberg .................................. 607/101 |
| 5,083,565 | 1/1992 | Parins . |
| 5,357,956 | 10/1994 | Nardella ................................... 128/642 |
| 5,383,874 | 1/1995 | Jackson et al. .............................. 606/1 |
| 5,579,764 | 12/1996 | Goldreyer ................................ 607/122 |
| 5,868,737 | 2/1999 | Taylor et al. .............................. 606/34 |
| 5,893,885 | 4/1999 | Webster, Jr. ............................. 607/122 |

FOREIGN PATENT DOCUMENTS

WO 95/10225  4/1995  WIPO .

Primary Examiner—Michael Peffley
Attorney, Agent, or Firm—Townsend and Townsend and Crew LLP

[57] ABSTRACT

The ablation catheter with a plurality of poles is used for the intracardial treatment of heart tissue. It has connectors for electrical connections to an HF generator and to an ECG measuring apparatus. At least two poles are connected via a condenser. This condenser is selected in such a manner that an HF energy output via the two poles and an ECG pickup between these two poles are possible at the same time.

13 Claims, 1 Drawing Sheet

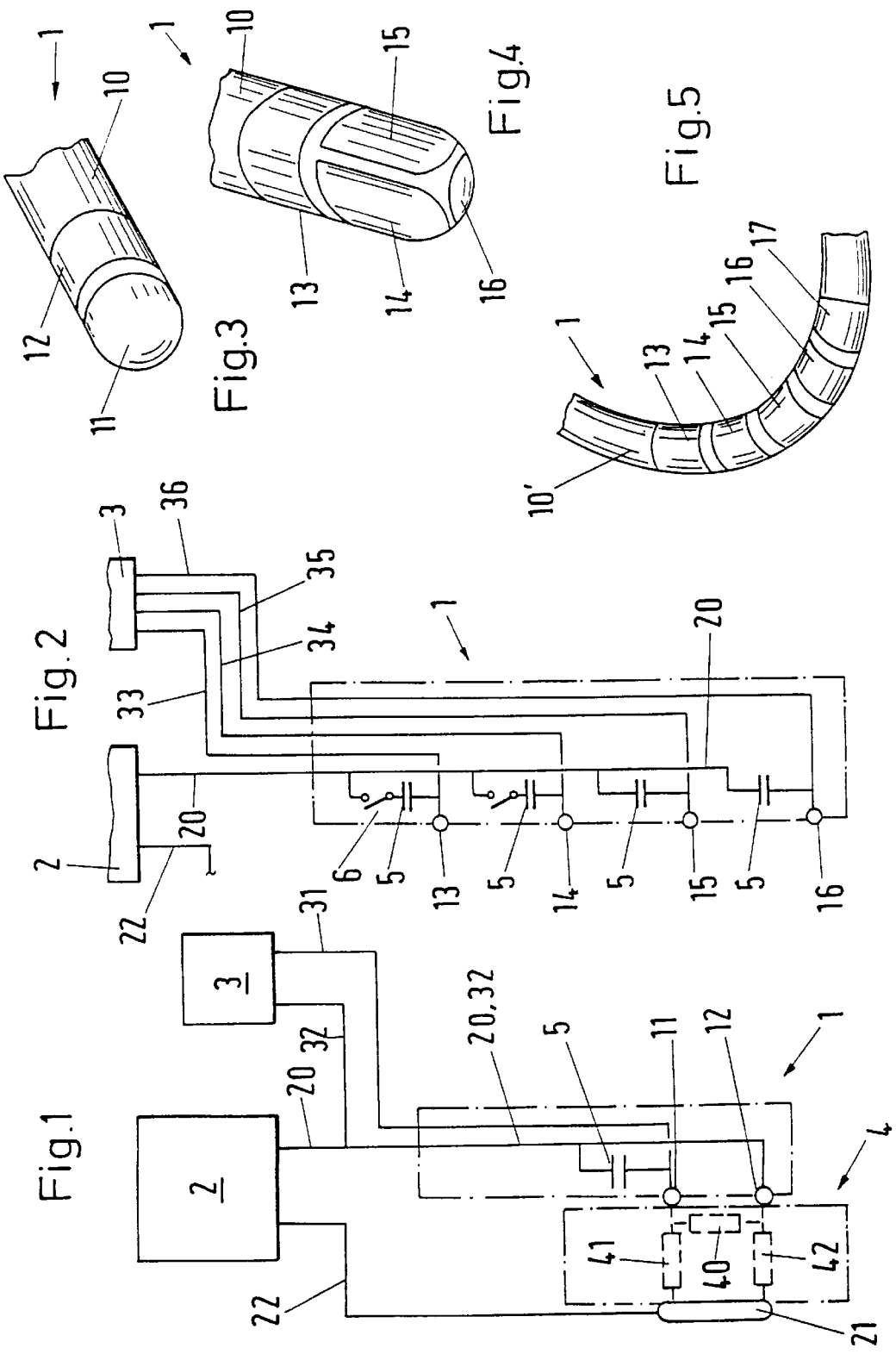

ABLATION CATHETER WITH A PLURALITY OF POLES

BACKGROUND OF THE INVENTION

The invention relates to an ablation catheter with a plurality of poles as well as to an ablation arrangement.

Ablation catheters of this kind are used for diagnostic and therapeutic purposes. On the one hand, signals belonging to the heart, namely ECG signals, can be picked up by the poles (diagnosis); on the other hand, ablations can be performed by means of HF energy outputs (therapy). During the ablation, a plurality of poles are advantageously connected together in order to achieve greater lesions. Switches are used for this purpose. After the switches have been closed, however, it is no longer possible to pick up an ECG signal between poles which have been short circuited by the switches.

In the case of certain heart rhythm disturbances, it is necessary to measure intracardial electrograms exactly in regions in which arrhythmias are triggered. In order to be able to detect the source of the arrhythmia exactly, catheters are provided with poles which mostly lie closely adjacent to one another. After a detection has taken place the poles which were used for the detection are used directly for the therapy in that HF energy is given off to the tissue for the purpose of thermal destruction. In order to produce larger lesions (e.g. linear or areal ones), the poles or some of the poles are short circuited through the closing of switches. In order to check on the success of the therapy using ECG measurements, the switches must be opened again.

SUMMARY OF THE INVENTION

The object of the invention is to provide an ablation catheter and an arrangement with a catheter of this kind which in a simple manner permits measurements of intracardial electrograms (ECG pickup) as well as HF energy outputs via a plurality of poles at the same time.

The ablation catheter of the invention having a plurality of poles is used for the intracardial treatment of heart tissue. It has connectors for an electrical connection to an HF or RF generator and to an ECG measuring apparatus. At least two poles are connected via a condenser. This condenser is selected in such a manner that an HF energy output via the two poles and an ECG pickup between these two poles are possible at the same time.

In accordance with the invention, condensers are connected between poles which are used for the ECG pickup and the HF energy output. Their capacitances are chosen in such a manner that, on the one hand, the condensers offer only a negligible reactance to the HF current to be transmitted to the tissue and, on the other hand, however, produce a sufficiently high resistance at low frequencies that the ECG pickup is not influenced.

In the ECG pickup the tissue resistance present between the poles is connected in parallel with the condenser and with the input impedance of the ECG measuring apparatus. The tissue resistance depends, among other things, on the size of the poles; it is on the order of magnitude of 100 to 300 ohms. The named input impedance is as a rule greater by at least three powers of ten and therefore need not be taken into consideration in selecting the capacitance of the condenser. The reactance of the condenser must be much greater at the ECG frequencies, i.e. up to about 500 Hz, than the resistance of the signal source, with this resistance being the tissue resistance. A condenser with a capacitance of, for example, 33 nF has a reactance of about $10^4$ ohms at 500 Hz, and thus lies more than a power of ten higher than the tissue resistance, and therefore has an acceptable value.

The HF current, having a frequency of about 500 kHz, is fed into the tissue by means of at least one catheter pole and a counter-electrode. For the tissue lying between the catheter pole and the counter-electrode, a resistance (likewise dependent on the pole size) of typically 100 ohms can be assumed. The condenser (33 nF) connected in series between the HF generator and the catheter pole has a reactance of about 10 ohms at the HF frequency, which is thus about an order of magnitude less than the tissue resistance. Since it is only a reactance, the HF generator must generate only slightly more power in order to transmit the same energy to the tissue as it would without the condenser being connected in series.

BRIEF DESCRIPTION OF THE DRAWINGS

FIG. 1 shows a schematic circuit diagram for an ablation arrangement in accordance with the invention, the catheter of which has two poles, FIG. 2 shows a schematic circuit diagram for a second embodiment of an ablation catheter in accordance with the invention, FIG. 3 shows the distal end of a catheter with two poles, FIG. 4 shows the distal end of a catheter with four poles, and FIG. 5 shows a section of a catheter in which poles are arranged in a region which is not located at the distal end.

DESCRIPTION OF THE PREFERRED EMBODIMENTS

The ablation arrangement of FIG. 1 comprises, in addition to an ablation catheter 1 in accordance with the invention (chain dotted rectangle), an HF generator 2 which is connected via a line 20 to the catheter 1 and via a line 22 to a counter-electrode 21 and an ECG measuring apparatus 3 which is in connection with the poles 11 and 12 of the catheter 1 via the lines 31 and 32 respectively. A tissue 4 to be treated is located between the poles 11 and 12 and the counter-electrode 21 (chain dotted rectangle). With respect to the ECG pickup a tissue resistance 40 is effective between the poles 11 and 12; with respect to the HF energy output the tissue resistances 41 and 42 are effective between the poles 11 and 12 on the one side and the counter-electrode 21 on the other side. As has already been mentioned above, the following order of magnitude values hold for the resistances: 100–300 ohms for the resistance 40, 100 ohms for each of the resistances 41 and 42.

In accordance with the invention a condenser 5 is arranged between the poles 11 and 12, for the capacitance of which a value of for example 33 nF is to be provided (see the above considerations). The connection 32 of the pole 12 to the ECG measuring apparatus 3 and the connection 20, via which the pole 12 is connected directly to the HF generator 2, are in part produced by a common length of line. The other pole 11 is connected via the condenser 5, which allows the HF current to pass through, and likewise via the line 20 to the HF generator 2 so that an HF energy output can take place via both poles 11 and 12 at the same time. At the lower frequencies of the ECG signal the condenser 5 largely separates the poles 11 and 12 so that intracardial electrograms can also be picked up by the ECG measuring apparatus 3 at the same time as the HF energy is being output.

In the catheter 1 illustrated in FIG. 2, all poles—namely the four poles 13, 14, 15 and 16—are connected via condensers 5 to the separate HF lead or feed line 20, which is connected to the HF generator 2 outside the catheter 1. In addition, the poles 13 to 16 are connected via pole leads 33, 34, 35 and 36 to the ECG measuring apparatus.

In the exemplary embodiment of FIG. 2 a condenser 5 is associated in accordance with the invention with each pole 13 to 16 provided for ECG pickups as well as for HF energy outputs, and each condenser 5 is connected to an HF lead 20 which is separately led to the pole leads or feed lines 33 to 36. It would also be possible that a condenser 5 is associated with each pole which is provided for ECG pickups as well as for HF energy outputs with the exception of only one pole and that the excepted pole is connected directly to the HF generator as well as to the ECG measuring apparatus. This is the case in the first exemplary embodiment, where the pole 12 forms this exception.

The second exemplary embodiment has the advantage over the first that the poles 13 to 16 behave symmetrically and that the coupling capacitance which is effective between the poles for the ECG pickup is in each case halved through the serial connection of two condensers 5.

Switches 6—see FIG. 2—can also be provided, by means of which selection can be made at the beginning of or during the treatment of the poles via which an HF output is to take place.

Obviously the catheter 1 can also have further poles which are not involved in the HF output and with which therefore no condensers 5 are associated.

As a rule the poles are arranged at the distal end 10 of the catheter 1 or near this end 10, as shown in FIG. 3 by a two-pole catheter 1 with a transversely divided tip or in FIG. 4 by a four-pole catheter 1 which has a triply longitudinally divided tip and a fourth pole arranged behind it. The exemplary embodiment of FIG. 5 illustrates a catheter 1 in which six poles 13 to 17 are arranged in a non-distal region 10' along the catheter. Naturally many other pole arrangements are also conceivable and realisable.

The condensers 5 are advantageously built into the catheter 1. They can in particular be arranged in a non-illustrated handle of the catheter.

The therapeutic success can be checked immediately with the apparatus in accordance with the invention during or directly after the ablation. No actuation of switches is required during the performance of the ablation, so that the apparatus is very easy to use.

I claim:

1. An ablation catheter for interacardial treatment of heart tissue, the ablation catheter comprising:
   a plurality of poles;
   at least one condenser; and
   electrical connections for coupling the poles to an HF generator and an ECG measuring apparatus,
   wherein at least two poles are adapted to be connected via a condenser which is selected so as to permit simultaneous generation of an HF energy output via said two poles and an ECG pickup between said two poles.

2. An ablation catheter in accordance with claim 1 wherein a condenser is adapted to be connected between each pole and the HF generator for providing HF energy output and ECG pickup.

3. An ablation catheter in accordance with claim 1 wherein a condenser is adapted to be connected between each pole and the HF generator for providing HF energy output and ECG pickup with exception of one pole, said one pole is adapted to be connected via electrical connections directly to the HF generator and to the ECG measuring apparatus.

4. An ablation catheter in accordance with claim 1 wherein the poles are arranged at or near a distal end of the catheter.

5. An ablation catheter in accordance with claim 1 including more than two poles, further comprising a switch associated with at least one of the poles, the switch adapted to be connected between the pole and the HF generator to permit interruption between the pole and the HF generator.

6. An ablation arrangement for interacardial treatment of heart tissue, the arrangement comprising:
   an HF generator;
   an ECG measuring apparatus; and
   an ablation catheter comprising a plurality of poles, at least one condenser, and electrical connections coupling the poles to an HF generator and an ECG measuring apparatus, at least two poles being connected via a condenser which is selected so as to permit simultaneous generation of an HF energy output via said two poles and an ECG pickup between said two poles.

7. An ablation arrangement in accordance with claim 6 wherein a condenser is connected between each pole and the HF generator for providing HF energy output and ECG pickup.

8. An ablation arrangement in accordance with claim 6 wherein a condenser is connected between each pole and the HF generator for providing HF energy output and ECG pickup with exception of one pole, said one pole being connected via electrical connections directly to the HF generator and to the ECG measuring apparatus.

9. An ablation arrangement in accordance with claim 6 wherein the poles are arranged at or near a distal end of the catheter.

10. An ablation arrangement in accordance with claim 6 wherein the catheter includes more than two poles, and further comprises a switch associated with at least one of the poles, the switch being connected between the pole and the HF generator to permit interruption between the pole and the HF generator.

11. An ablation arrangement in accordance with claim 6 wherein the condenser is built into the catheter.

12. An ablation arrangement in accordance with claim 6 wherein the condenser is built into a handle of the catheter.

13. A method of interacardial treatment of heart tissue, the method comprising:
   providing an ablation catheter including a plurality of poles;
   electrically coupling the poles to an HF generator and an ECG measuring apparatus; and
   connecting at least two poles via a condenser to simultaneously generate an HF energy output via said two poles and an ECG pickup between said two poles.

* * * * *